(12) United States Patent
Chang et al.

(10) Patent No.: US 8,586,635 B2
(45) Date of Patent: Nov. 19, 2013

(54) ANTIFUNGAL COMPOSITIONS FOR INHIBITING GROWTH OF WOOD DECAY FUNGI AND USE THEREOF

(75) Inventors: Shang-Tzen Chang, Taipei (TW); Fu-Lan Hsu, Taipei (TW); Hui-Ting Chang, Taipei (TW); Tsair-Bor Yen, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/211,563

(22) Filed: Aug. 17, 2011

(65) Prior Publication Data

US 2011/0301246 A1 Dec. 8, 2011

Related U.S. Application Data

(63) Continuation-in-part of application No. 11/944,047, filed on Nov. 21, 2007, now abandoned.

(51) Int. Cl.
*A01N 35/02* (2006.01)
*A01N 31/14* (2006.01)

(52) U.S. Cl.
USPC ............ 514/701; 514/703; 514/717; 514/720

(58) Field of Classification Search
USPC .................................. 514/703, 717, 720, 701
See application file for complete search history.

(56) References Cited

U.S. PATENT DOCUMENTS 4,978,686 A * 12/1990 Sotome .......................... 514/698
2008/0132569 A1 * 6/2008 Chang et al. ................... 514/532

OTHER PUBLICATIONS

Wang, Sheng-Yang et al., "Antifungal activities of essential oils and their constituents from indigineous cinamon . . . " Bioresource Technology, vol. 96, pp. 813-818 (2005).*
HCAPLUS abstract 1961:66970 (1961).*
Derwent abstract 2004-028076; abstracting JP 2003/334804 (2003).*

* cited by examiner

*Primary Examiner* — John Pak
(74) *Attorney, Agent, or Firm* — WPAT, P.C.; Anthony King

(57) ABSTRACT

The present invention is related to an antifungal composition for the inhibition of wood decay caused by wood rot fungi. The invention further comprises a method for the inhibition of wood decay with gallates.

2 Claims, 4 Drawing Sheets

ANTIFUNGAL COMPOSITIONS FOR INHIBITING GROWTH OF WOOD DECAY FUNGI AND USE THEREOF

CROSS-REFERENCE TO RELATED APPLICATIONS

This application is a Continuation-in-part of the pending U.S. patent application Ser. No. 11/944,047 filed on Nov. 21, 2007, that is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention is related to the field of an antifungal composition for the inhibition of lignocellulosic material decay. This invention further relates to a method for the inhibition of lignocellulosic material decay.

BACKGROUND OF THE INVENTION

Lignocellulosic material possesses many good characteristics and has been utilized widely in our daily life since ancient time. Lignocellulosic material is defined as wood products, furniture, wooden objects, wood composites, wood-based cultural relics, paper and paper board, paper-based materials, paper-based cultural relices, bamboo products, bamboo-based cultural relics. Wood composed of cellulose, hemicelluloses, and lignin, not only provides a good nutritional source for microbes and insects but also a suitable habitat because of its hydrophilic functional group and porous property. Under warm and humid climatic conditions in the world, lignocellulosic material is very easy to be attacked by living creatures, especially various fungi, causing huge impact on economy and natural resource loss.

In order to extend the servicelife of lignocellulosic products, various preservatives have been developed for treating lignocellulosic material. Due to the elevation of environmental awareness, most of the widely used preservatives could not meet users' expectation. A great preservative, chromated copper arsenate (CCA) compounds, is under strict regulation of production and application in many countries due to its heavy metal content such as chromium and arsenate which are human carcinogens as well as environmental pollutants. Currently, most alternative preservatives of CCA still use heavy metal copper (copper-organic mixture) for its anti-microorganism activity, such as alkaline copper quaternary ammonium compounds (ACQ), or ammoniacal copper azole (CuAz) compounds. Although the heavy metal of these compounds is less toxic, the impact to our environment still comes along with its waste. It all adds up to the processing cost eventually. These alternative preservatives of CCA also have some disadvantages such as highly corrosive to metal equipments. Besides, some strains of fungi causing wood damage are highly tolerant to copper. Therefore, the latest preservatives still cannot inhibit lignocellulosic material decay completely.

In order to eliminate the disadvantages of current preservatives such as non-environmental friendliness and inability to inhibit copper tolerant fungi, this invention provides an environmental friendly method and composition to inhibit lignocellulosic material decay caused by fungal infection.

SUMMARY OF THE INVENTION

The present invention relates to a chemical composition for the inhibition of lignocellulosic material decay caused by fungal infection.

This invention further comprises a method of application of an antifungal composition for the inhibition of lignocellulosic material decay, especially caused by wood decay fungi.

DETAILED DESCRIPTION OF THE INVENTION

Figure 1:
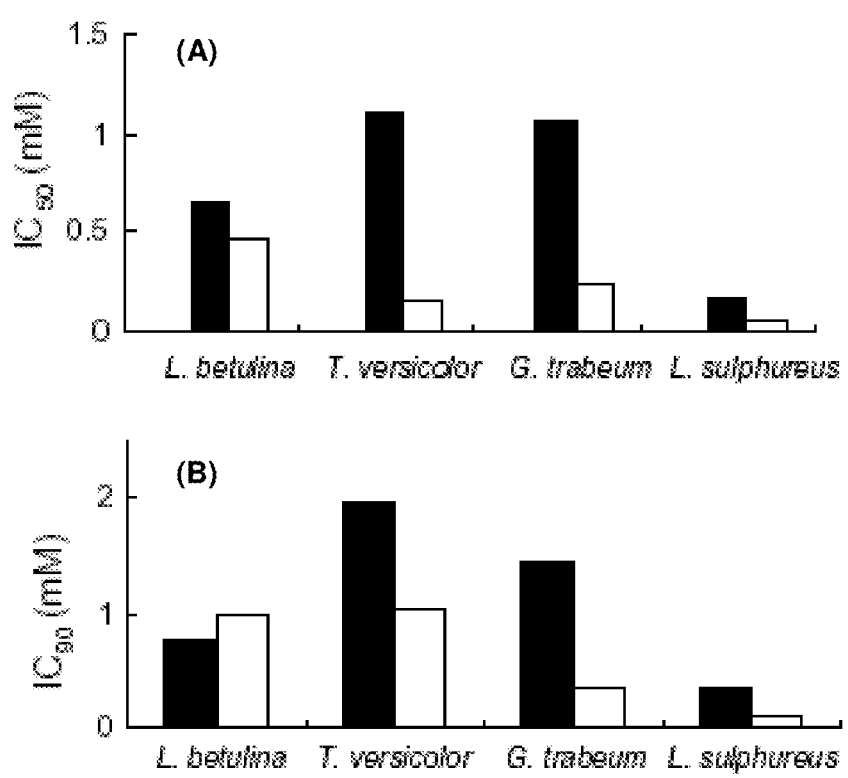
FIG. 1 shows the inhibition effect of cinnamaldehyde (black bar) and octyl gallate (white bar) against four strains of wood decay fungi: *L. betulina*, *T. versicolor*, *G. trabeum* and *L. sulphureus*. (A) a bar graph indicating $IC_{50}$ value (the concentration in that inhibited 50% of the mycelium growth). (B) a bar graph indicating $IC_{90}$ value (the concentration in that inhibited 90% of the mycelium growth).

The purpose of the present invention is to provide an environmental friendly composition which does not contain chromium, arsenate or copper and can be used as a wide spectrum lignocellulosic material preservative against various lignocellulosic material decay fungi. Most of the microbes that cause lignocellulosic material decay described in the present invention belong to the phyla Basidiomycota and Ascomycota. They are further classified as brown-rot fungi such as *Coriolelus palustris* (JIS), *Coniophora puteana* (EN), *Poria placenta* (ASTM), *Paxillus panuoides* and *Serpula lacrymans*; white-rot fungi such as *Bjerkanderna adusta*, *Ceraceomerulius serpens*, *Phanerochaete chrysosporium*, *Phlebiopsis gigantean*, *Schizophyllum commune* and *Phlebia subseralis*; and soft rot fungi such as *Aspergillus terreus*, *Aspergillus niger*, *Chaetomium globosum*, *Myrothecium verrucaria*, *Trichoderma lignorum*, *Penicillium citrinum*, *Aspergillus clavatus* and *Memnoniella echinata*.

The problems of current lignocellulosic material preservatives are causing environmental pollution and their inability to inhibit copper tolerant wood decay fungi. The present invention provides a solution to solve these problems. This invention provides an antifungal composition for the inhibition of lignocellulosic material decay, which comprises application of low toxic alkyl gallates alone or combined with compounds such as cinnamaldehyde or diaminoethanetetraacetic acid (EDTA) as a mixture to inhibit the growth of various wood decay fungi. This invention provides an antifungal composition for the inhibition of lignocellulosic material decay, which comprises application of cinnamaldehyde or similar compounds alone or combined with compounds such as eugenol or EDTA. These compounds are dissolved in organic solvent such as ethanol.

The mycelium growth of lignocellulosic material decay fungi can be inhibited after treating with alkyl gallate alone or that with compounds such as cinnamaldehyde or EDTA as well as treating with cinnamaldehyde or similar compounds alone or that with eugenol or EDTA. The present invention can serve as an excellent alternative chemical composition to decrease the demand of current heavy metal wood preservatives and to alleviate the environmental impact. Also, this invention can inhibit copper tolerant wood decay fungi which can not be achieved by current heavy metal wood preservatives.

Accordingly, the present invention relates to an antifungal composition for the inhibition of lignocellulosic material decay, comprising a compound of formula I:

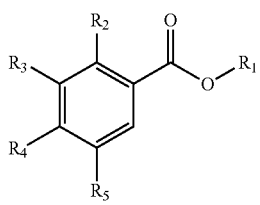

I wherein $R_1$ is $(CH_2)_n CH_3$, n=2~11; $R_2$ is H or OH; $R_3$ is $OCH_3$, H or OH; $R_4$ is $OCH_3$, H or OH; and $R_5$ is H or OH.

In preferred embodiment, the compound of formula I wherein n=7; $R_2$ is H; $R_3$ is OH; $R_4$ is OH and $R_5$ is OH.

In another preferred embodiment, the compound of formula I wherein n=2; $R_2$ is H; $R_3$ is OH; $R_4$ is OH and $R_5$ is OH.

The composition can further comprise cinnamaldehyde or EDTA in addition to the compound of formula I and result in synergistic antifungal effect.

The compound of formula I is dissolved in an organic solvent. In preferred embodiments, the organic solvent is ether or alcohol such as ethanol and the compound is dissolved to obtain the final concentration of 0.5~1000 µg/ml.

The present invention also relates to an antifungal composition for the inhibition of lignocellulosic material decay, comprising a compound of formula II

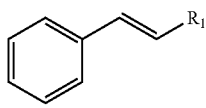

II wherein $R_1$ is $CH_2OH$, $CH_2OCOCH_3$, CHO or COOH.

In preferred embodiment, the compound of formula II wherein $R_1$ is CHO.

The composition can further comprise eugenol or EDTA in addition to the compound of formula II and result in synergistic antifungal effect.

In a preferred embodiment, the fungal infection is caused by Laetiporus sulphureus.

The present invention also relates to a method for the inhibition of lignocellulosic material decay caused by fungal infection, which comprises administering to a lignocellulosic material an effective amount of a composition, comprising a compound of formula I

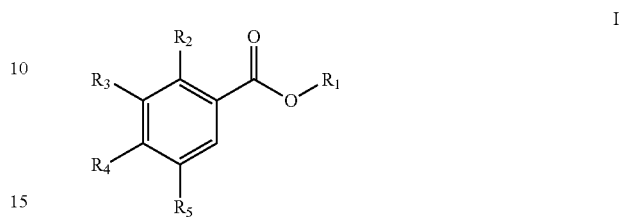

I wherein $R_1$ is $(CH_2)_n CH_3$, n=2~11; $R_2$ is H or OH; $R_3$ is $OCH_3$, H or OH; $R_4$ is $OCH_3$, H or OH; and $R_5$ is H or OH.

In preferred embodiments, wherein n=7; $R_2$ is H; $R_3$ is OH; $R_4$ is OH; and $R_5$ is OH.

In another preferred embodiments, wherein n=2; $R_2$ is H; $R_3$ is OH; $R_4$ is OH; and $R_5$ is OH.

The composition can further comprise cinnamaldehyde or EDTA in addition to the compound of formula I and result in synergistic antifungal effect.

In preferred embodiments, wherein the lignocellulosic material is an antique made by lignocellulosic materials.

In the present invention the fungal infection is mostly caused by fungi in the phyla of Basidiomycota or Ascomycota.

In a preferred embodiment, the fungal infection is caused by Laetiporus sulphureus.

The present invention also relates to a method for the inhibition of lignocellulosic material decay caused by fungal infection, which comprises administering to a lignocellulosic material an effective amount of a composition, comprising a compound of formula II

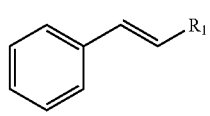

II wherein $R_1$ is $CH_2OH$, $CH_2OCOCH_3$, CHO or COOH.

In preferred embodiments, wherein $R_1$ is CHO.

The composition can further comprise eugenol or EDTA in addition to the compound of formula II and result in synergistic antifungal effect.

In preferred embodiments, wherein the lignocellulosic material is an antique made by lignocellulosic materials.

In preferred embodiments, wherein the fungal infection is caused by fungi in the phyla of Basidiomycota or Ascomycota.

The effective amount of the chemical composition of the present invention is alkyl gallate at a concentration of 0.5~4000 µg/ml. A suitable application is to dissolve alkyl gallate in organic solvent. A more suitable application is to dissolve alkyl gallate in alcohol or ether. The most suitable application is to dissolve alkyl gallate in ethanol.

In preferred embodiments, the chemical composition of alkyl gallate further comprises disinfectant, such as cinnamaldehyde, eugenol, alpha-cadinol, carvacrol, T-muurolol, T-cadinol, gamma-cadinene, cyptomeridiol, tropolones, pinosylvin, resveratrol, dihydromorin, and/or ferruginol.

In preferred embodiments, the chemical composition of alkyl gallate may also comprise antioxidant or metal chelator. The following examples illustrate the present inventions and are not limited to the same.

EXAMPLES

Example 1

Antifungal Activity of Antioxidants (Propyl Gallate, Octyl Gallate and Butylated Hydroxyltoluene) and Cinnamaldehyde Fungal Strains Fungal strains used were two white-rot fungi: *Lenzites betulina* (BCRC 35296) and *Trametes versicolor* (BCRC 35253) and two brown-rot fungi: *Laetiporus sulphureus* (BCRC 35305) and *Gloeophyllum trabeum* (BCRC 31614).
Chemicals Propyl gallate and octyl gallate were purchased from Tokyo Kasei Kogyo Co. (Japan). Butylated hydroxyltoluene (BHT) and 1-diphenyl-2-picrylhydrazyl (DPPH) were purchased from Sigma Chemical Co. (America). Cinnamaldehyde was purchased from ACROS (Belgium). Commercial fungicide propiconazole was used as a positive control.
Media Preparation and Growth Condition Potato dextrose agar (PDA) was mixed with distilled water at a concentration of 39 g/l and then autoclaved. Various chemicals such as propiconazole, propyl gallate, octyl gallate and cinnamaldehyde were dissolved in ethanol before adding into autoclaved PDA media.

After transferring the mycelia of fungal strains onto PDA containing various chemicals, the media were incubated in the dark at 27±2° C. and with 70% relative humidity till the fungal mycelium reached the edges of the control dishes.
Antifungal Assays Antifungal assays were performed based on Chang et al. (Holzforschung 1999, 53:487-490; Holzforschung 2000, 54:241-245) with slight modifications. Propiconazole, cinnamaldehyde, propyl gallate and octyl gallate were dissolved in ethanol; BHT was dissolved in ethanol containing 1% Tween. Chemicals were added into autoclaved PDA media at various concentrations. When the mycelium of fungi reached the edges of the control dishes, the antifungal indices (AI %) were calculated. Each test was repeated three times and the average was calculated. The formula to calculate antifungal index was shown as follows:

Antifungal index (AI, %)=(1−Da/Db)×100

Da is the diameter of growth zone in the experimental dish (cm) and Db is the diameter of growth zone in the control dish (cm).

The $IC_{50}$ values (the concentration in that inhibited 50% of the mycelium growth) were calculated by probit analysis.

The $IC_{90}$ values (the concentration in that inhibited 90% of the mycelium growth) were calculated by probit analysis.
Antifungal Index (%) of Test Compounds Against Four Wood Decay Fungi The antifungal activities of samples are shown in Table 1. Among all samples tested, the commercial fungicide, propiconazole, was the most effective with an antifungal index of 100% against *L. betulina* and *L. sulphureus* at the concentration of 1 μg/ml. At the concentration of 100 μg/ml, octyl gallate exhibited stronger antifungal activity against all fungi than other two antioxidants, propyl gallate and BHT. Octyl gallate also exhibited stronger antifungal activity against *T. versicolor*, *G. trabeum* and *L. sulphureus* than cinnamaldehyde.

TABLE 1

Antifungal index (%) of test compounds against four wood decay fungi at the concentration of 100 μg/ml

| Compounds | Wood decay fungi | | | |
| --- | --- | --- | --- | --- |
| | *L. betulina* | *T. versicolor* | *G. trabeum* | *L. sulphureus* |
| Propiconazole[a] | 100 ± 0 | 92 ± 0.6 | 52 ± 3.7 | 100 ± 0 |
| Cinnamaldehyde | 100 ± 0 | 34 ± 2.2 | 31 ± 0.7 | 100 ± 0 |
| Octyl gallate | 43 ± 2.5 | 69 ± 9.1 | 85 ± 26.2 | 100 ± 0 |
| Propyl gallate | 1 ± 1.9 | 0 ± 0 | 2 ± 0.6 | 0 ± 0 |
| BHT | 16 ± 3.4 | 23 ± 2.6 | 0 ± 0 | 21 ± 5.6 |

[a]The concentration of propiconazole was 1 μg/ml.

$IC_{50}$ and $IC_{90}$ value of cinnamaldehyde or octyl gallate against four wood decay fungi The $IC_{50}$ and $IC_{90}$ values obtained for octyl gallate and cinnamaldehyde against four decay fungi are shown in FIG. 1. The $IC_{50}$ values of cinnamaldehyde were 0.65, 1.11, 1.05, and 0.17 mM against *L. betulina*, *T versicolor*, *G. trabeum* and *L. sulphureus*, respectively, while the $IC_{50}$ values of octyl gallate against these four fungi was 0.47, 0.16, 0.24 and 0.04 mM, respectively [FIG. 1(A)]. This result clearly showed that octyl gallate had better antifungal property than cinnamaldehyde. As for $IC_{90}$, octyl gallate was also more effective than cinnamaldehyde for growth inhibition of *T. versicolor*, *G. trabeum* and *L. sulphureus*, but not for *L. betulina* [FIG. 1(B)].

Example 2

Antifungal Activity of Octyl Gallate Alone

The strains used in this experiment include soft rot fungi [*Chaetomium globosum* (BCRC31605)], Cu tolerant rot fungi [*Wolfiporia extensa* (BCRC36022), *Poria placenta* (BCRC36412)], brown rot fungi [*Laetiporus sulphureus* (BCRC35305), *Gloeophyllum trabeum* (BCRC31614), *Fomitopsis pinicola* (BCRC35303), *Antrodia taxa*] and white rot fungi [*Lenzites betulina* (BCRC35296), *Trametes versicolor* (BCRC35253), *Schizophyllum commune* (BCRC35258)].

The antifungal index (AI %) and median inhibition concentration ($IC_{50}$) were measured as described before.

As shown of AI values in Table 2 and $IC_{50}$ values in Table 3, at the concentration of 100 μg/ml, octyl gallate could inhibit the growth of *C. globosum* and *A. taxa* completely, while showing 75~96% inhibition against *W. extensa*, *P. placenta*, *L. sulphureus*, *G. trabeum* and *F. pinicola*. Octyl gallate also showed 41~69% inhibition ability against *L. betulina*, *T. versicolor* and *S. commune* at the concentration of 100 μg/ml. The $IC_{50}$ values of octyl gallate against soft rot, Cu tolerant, and brown rot fungi was less than 50 μg/ml; the $IC_{50}$ value of octyl gallate against white rot fungi was also less than 200 μg/ml. These observations indicate that octyl gallate inhibits a wide variety of wood rot fungi. Octyl gallate can not only extend its lifespan of wood product but also meet the environmental standard because of its low toxicity to the environment and human beings.

TABLE 2

Antifungal index (%) of octyl gallate against various fungal strains at different concentrations (μg/ml)

| | Soft rot fungi | Cu tolerant fungi | | Brown rot fungi | | | | White rot fungi | | |
|---|---|---|---|---|---|---|---|---|---|---|
| Conc. | C. globosum | W. extensa | P. placenta | L. sulphureus | G. trabeum | F. pinicola | A. taxa | L. betulina | T. versicolor | S. commune |
| 25  | 82  | 3  | 58 | —   | —  | 52  | 73  | 16 | 37 | 16 |
| 50  | 100 | 50 | 75 | 85  | 49 | 78  | 100 | 28 | 50 | 40 |
| 100 | 100 | 75 | 82 | 96  | 77 | 94  | 100 | 41 | 69 | 60 |
| 200 | 100 | 64 | 84 | 100 | 93 | 100 | 100 | 88 | 85 | 83 |

TABLE 3

$IC_{50}$ value (μg/ml) of octyl gallate against various wood decay fungi

| Soft rot fungi | Cu tolerant fungi | | Brown rot fungi | | | | White rot fungi | | |
|---|---|---|---|---|---|---|---|---|---|
| C. globosum | W. extensa | P. placenta | L. sulphureus | G. trabeum | F. pinicola | A. taxa | L. betulina | T. versicolor | S. commune |
| <25 | 50 | <25 | 50.6 | 50.8 | <25 | <25 | 137.6 | 173 | 114 |

Example 3

Figure 2:
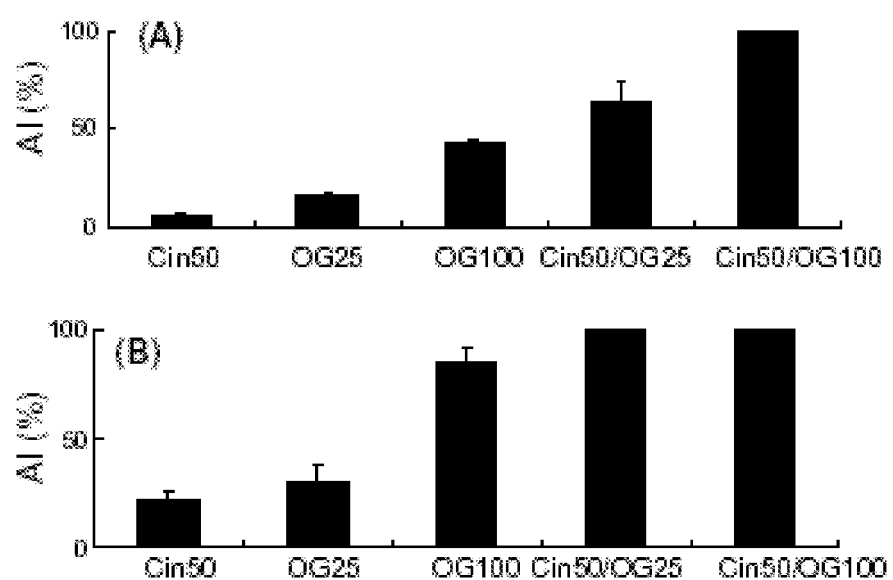
FIG. 2 shows the antifungal activity of cinnamaldehyde and/or octyl gallate against two strains of wood decay fungi: (A) *L. betulina*, and (B) *G. trabeum*. Cin50: cinnamaldehyde at the concentration of 50 µg/ml. OG25: octyl gallate at the concentration of 25 µg/ml. OG100: octyl gallate at the concentration of 100 µg/ml.
Figure 3:
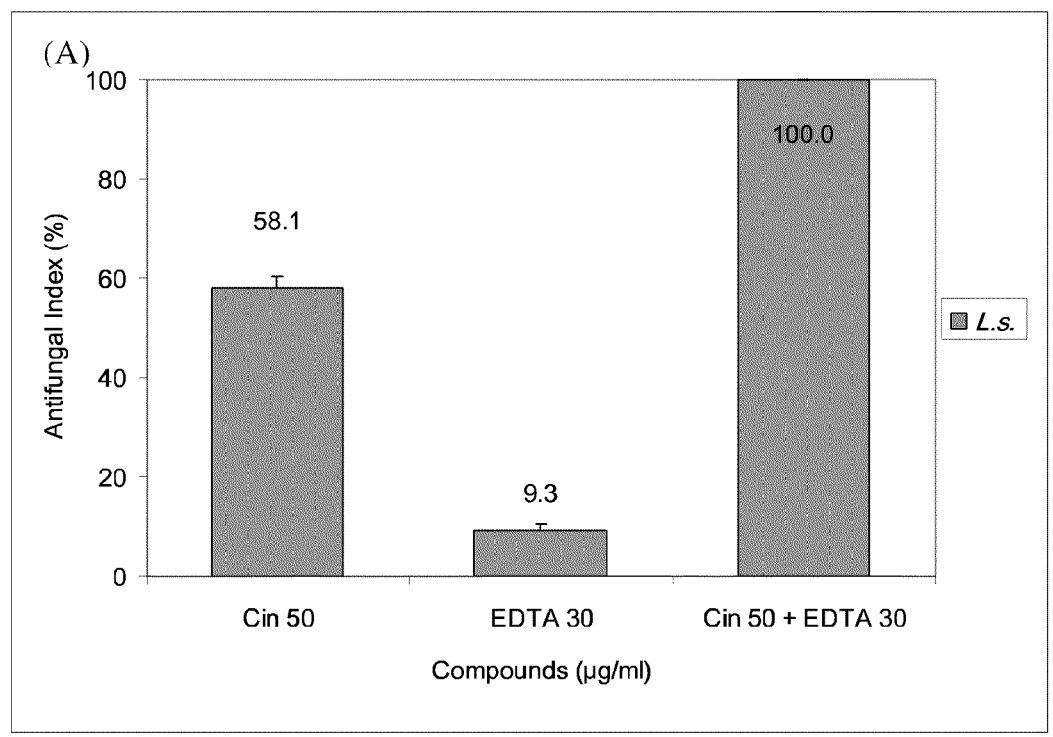
FIG. 3 shows the antifungal activity of cinnamaldehyde and/or EDTA against (A) *L. sulphureus* and (B) *L. betulina*. Cin50: cinnamaldehyde at the concentration of 50 µg/ml. EDTA30: EDTA at the concentration of 30 µg/ml.
Figure 3:
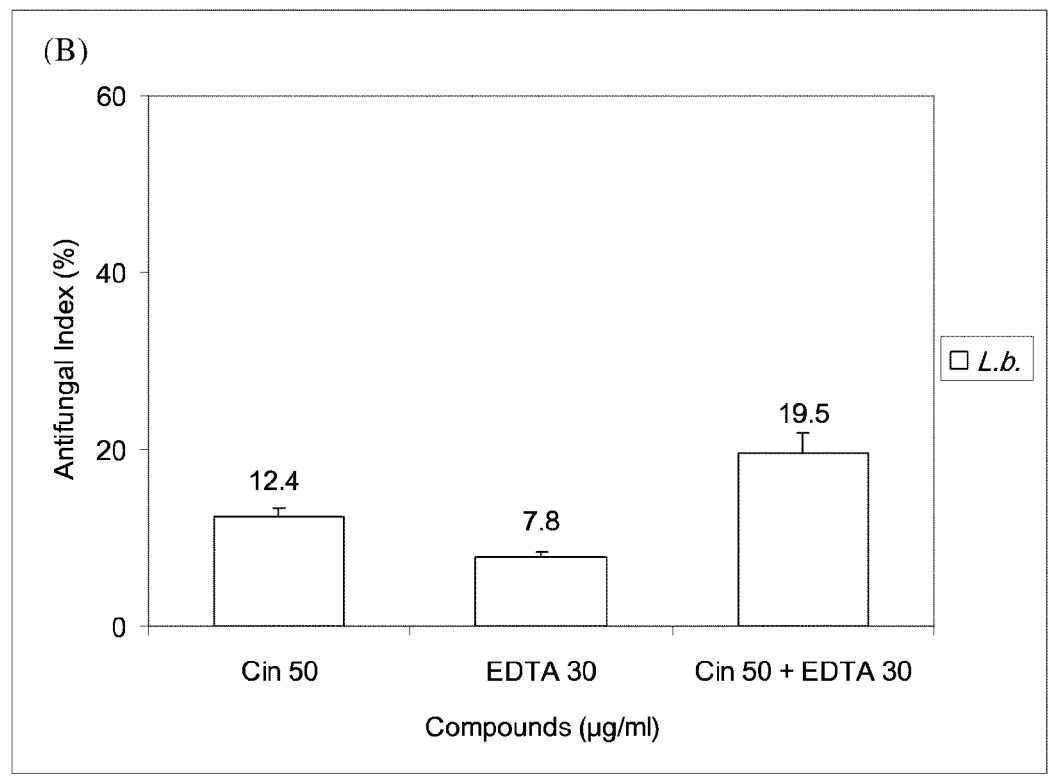

Synergistic Antifungal Effects of the Combination of Octyl Gallate with Cinnamaldehyde Antioxidants combined with cinnamaldehyde were studied to determine whether the combination has enhanced actions against wood decay fungi. The antifungal index (AI %) was calculated as described above. As shown in FIG. 2, the tested fungi were L. betulina (A) and G. trabeum (B). Octyl gallate (OG) and/or cinnamaldehyde (Cin) were used to treat wood decay fungi in various combinations. Cin50 indicated the concentration of cinnamaldehyde was 50 μg/ml, and OG25 indicated the concentration of octyl gallate was 25 μg/ml.

The antifungal index of cinnamaldehyde against L. betulina at the concentration of 50 μg/ml was 6% and that of octyl gallate against L. betulina at the concentration of 25 and 100 μg/ml was 16% and 42%, respectively. The antifungal index for the treatment using the combination of cinnamaldehyde with octyl gallate was greatly increased to 64% and 100%, respectively, indicating that the cinnamaldehyde/octyl gallate combination had significant synergism against L. betulina.

The same synergistic effect was also observed for G. trabeum. The antifungal index of cinnamaldehyde against G. trabeum at the concentration of 50 μg/ml was 22% and that of octyl gallate against G. trabeum at the concentration of 25 μg/ml was 30%. The antifungal index for the treatment using the combination of cinnamaldehyde with octyl gallate was greatly increased to 100%. In other words, the combination of octyl gallate and cinnamaldehyde has great inhibition effect against wood decay fungi. The combination can reach the similar effect even with less amounts of chemicals. Besides, wood treatment with low toxic octyl gallate and cinnamaldehyde can not only extend the lifespan of wood products, but also meet our need for the environment and public health.

Example 4

Synergistic Antifungal Effect of Cinnamaldehyde in Combination with Eugenol Against Wood Decay Fungi The fungal strains used were white-rot fungus, Lenzites betulina (BCRC 35296) and brown-rot fungus, Laetiporus sulphureus (BCRC 35305). 1-Diphenyl-2-picrylhydrazyl (DPPH) and ascorbic acid were purchased from Sigma Chemical Co. (USA). Cinnamaldehyde, eugenol, catechin and quercetin were purchased from ACROS (Belgium). Commercial fungicide propiconazole was used as a positive control.

Antifungal assays were performed as described before with slight modifications. Cinnamaldehyde, catechin, quercetin, eugenol and propiconazole were dissolved in ethanol. Solutions of serial concentrations of chemicals were mixed with sterilized potato dextrose agar (PDA) in Petri dish (9 cm dia.) containing 15 ml agar. After inoculating the mycelia of fungus onto the center of agar, the dishes were incubated in the dark at 27±2° C. and 70% relative humidity. When the mycelium of fungi reached the edges of the control dishes, the antifungal indices were calculated as described before.

Minimal inhibitory concentrations (MICs) were also examined using the methods reported by Kubo and Lee (J. Agric. Food Chem. 1998, 46:4052-4055) with slight modifications. The testing dishes were incubated under the same growth conditions as above. When the mycelium of fungi reached the edges of the control dishes, the lowest concentration with no sign of growth was defined as MIC. After the MIC was determined, a small piece of agar ($2\times2\times2$ mm$^3$) was taken from the colony of the MIC plate, and was inoculated on a drug-free PDA medium. After 5 days, minimum fungicidal concentrations (MFCs) were determined by the lowest concentration of the test compounds in which no recovery of microorganism was observed.

The antifungal activities of test compounds were first examined at the concentration of 100 μg/ml, and the results are shown in Table 4. Among all compounds tested, the commercial fungicide, propiconazole, was the most effective and completely inhibited the growth of L. betulina and L. sulphureus at the concentration of 1 µg/ml. Cinnamaldehyde and eugenol also exhibited strong antifungal activities with antifungal index of 100% against both L. betulina and L. sulphureus, while catechin and quercetin did not express antifungal activities at the same concentration.

TABLE 4

Antifungal index (%) of test compounds against wood decay fungi at the concentration of 100 µg/ml

| | Fungi | |
|---|---|---|
| Compounds | L. betulina | L. sulphureus |
| Cinnamaldehyde | 100 ± 0.0$^a$ | 100 ± 0.0$^a$ |
| Catechin | 3 ± 1.5$^b$ | 5 ± 1.8$^b$ |
| Quercetin | 0 ± 0.0$^b$ | 0 ± 0.0$^c$ |
| Eugenol | 100 ± 0.0$^a$ | 100 ± 0.0$^a$ |
| Propiconazole* | 100 ± 0.0$^a$ | 100 ± 0.0$^a$ |

*Concentration of propiconazole was 1 µg/ml as a positive control. Results are mean ± SE (n = 5). Means with different superscript letters are significant different at alpha level of 0.05.

The $IC_{50}$ and $IC_{90}$ values for individual compound were further determined, and the results obtained for cinnamaldehyde, eugenol, catechin and quercetin against two wood decay fungi are shown in Table 5. The $IC_{50}$ values of cinnamaldehyde were 0.65 and 0.23 mM against L. betulina and L. sulphureus, respectively. Among these three antioxidants, only eugenol showed excellent antifungal activities against L. betulina and L. sulphureus with $IC_{50}$ of 0.37 and 0.25 mM, respectively. On the contrary, catechin and quercetin revealed very limited inhibitory effects against L. betulina and L. sulphureus. As for $IC_{90}$, the similar results were found that both cinnamaldehyde and eugenol exhibited much stronger antifungal activities against L. betulina and L. sulphureus than those of catechin and quercetin.

TABLE 5

$IC_{50}$ and $IC_{90}$ values of test compounds and in combinations with cinnamaldehyde against wood decay fungi

| | L. betulina | | L. sulphureus | |
|---|---|---|---|---|
| Compounds | $IC_{50}$ (mM) | $IC_{90}$ (mM) | $IC_{50}$ (mM) | $IC_{90}$ (mM) |
| Cinnamaldehyde | 0.65 ± 0.03$^b$ | 0.72 ± 0.06$^b$ | 0.23 ± 0.02$^b$ | 0.53 ± 0.02$^b$ |
| Eugenol | 0.37 ± 0.02$^a$ | 0.65 ± 0.05$^a$ | 0.25 ± 0.03$^b$ | 0.52 ± 0.01$^b$ |
| Catechin | >100$^e$ | >100$^e$ | 40 ± 0.12$^c$ | 80 ± 0.14$^c$ |
| Quercetin | >100$^e$ | >100$^e$ | 64 ± 0.25$^d$ | >100$^d$ |
| Cin. + eugenol | 0.38 ± 0.02$^a$ | 0.63 ± 0.04$^a$ | 0.18 ± 0.01$^a$ | 0.37 ± 0.02$^a$ |
| Cin. + catechin | 1.22 ± 0.04$^c$ | 1.40 ± 0.09$^c$ | 0.23 ± 0.04$^b$ | 0.52 ± 0.04$^b$ |
| Cin. + quercetin | 1.44 ± 0.06$^d$ | 1.65 ± 0.07$^d$ | 0.26 ± 0.02$^b$ | 0.53 ± 0.03$^b$ |

Results are mean ± SE (n = 5). Means in column with different superscript letters are significant different at alpha level of 0.05. Cin.: cinnamaldehyde.

The combined effects of cinnamaldehyde with eugenol, catechin or quercetin were evaluated by comparing the isoeffective concentrations ($IC_{50}$ and $IC_{90}$) of test compounds and designated combinations. It was considered synergy when the isoeffective concentration of combination was significantly lower than those of compounds acting alone. Cinnamaldehyde with eugenol, catechin or quercetin were prepared at 1:1 ratio in molarities with serial concentrations for assaying, and the values of $IC_{50}$ and $IC_{90}$ were given in Table 5.

Significant synergy was observed on the combination of cinnamaldehyde with eugenol against L. sulphureus. The antifungal index of cinnamaldehyde against L. sulphureus at the concentration of 0.17 mM was 41%, and that of eugenol at the same concentration was 24%, while the antifungal index of combination using cinnamaldehyde and eugenol against L. sulphureus dramatically increased to 90%, indicating portent of synergistic effect. The synergy was further confirmed by comparing their isoeffective concentrations. The values of $IC_{50}$ and $IC_{90}$ for the combination of cinnamaldehyde with eugenol against L. sulphureus were 0.18 and 0.37 mM, respectively, which were significantly lower than those of using either cinnamaldehyde or eugenol alone. However, only additive effect was found on the combination of cinnamaldehyde and eugenol against L. betulina with $IC_{50}$ (0.38 mM) and $IC_{90}$ (0.63 mM). In addition, the combinations of cinnamaldehyde with catechin or quercetin against L. sulphureus also exhibited additive effects, but both combinations showed marked antagonistic effects against L. betulina. The values of $IC_{50}$ and $IC_{90}$ for the combination of cinnamaldehyde with catechin against L. betulina were 1.22 and 1.40 mM, and against L. sulphureus were 0.23 and 0.52 mM, respectively. Among all samples tested, the strongest antagonistic effect was discovered on the combination of cinnamaldehyde and quercetin against L. betulina with $IC_{50}$ (1.44 mM) and $IC_{90}$ (1.65 mM) which were significantly higher than those of cinnamaldehyde alone.

Furthermore, the values of MIC and MFC for cinnamaldehyde and eugenol alone and their combination were determined. The results, as seen in Table 6, showed that strong synergism was also observed for the combination of cinnamaldehyde and eugenol against L. sulphureus with significantly lower values of MIC (0.40 mM) and MFC (0.40 mM) than that of cinnamaldehyde or eugenol alone. However, this combination only revealed additive effect against L. betulina with MIC (0.68 mM) and MFC (0.68 mM) which were no different to MIC and MFC values of cinnamaldehyde or eugenol. The same values of MIC and MFC for the combination of cinnamaldehyde with eugenol also showed it was fungicidal instead of fungistatic.

From the results, it could be concluded that the combination of cinnamaldehyde with eugenol showed excellent antifungal properties, and the strong synergy was also observer against L. sulphureus on the basis of $IC_{50}$, $IC_{90}$, MIC or MFC.

TABLE 6

MIC and MFC values of cinnamaldehyde, eugenol and their combination against two wood decay fungi

| | L. betulina | | L. sulphureus | |
|---|---|---|---|---|
| Compounds | MIC (mM) | MFC (mM) | MIC (mM) | MFC (mM) |
| Cinnamaldehyde | 0.75 | 0.75 | 0.70 | 0.70 |
| Eugenol | 0.70 | 0.70 | 0.65 | 0.65 |
| Cin. + eugenol | 0.68 | 0.68 | 0.40 | 0.40 |

Cin.: cinnamaldehyde.

Example 5

Synergistic Antifungal Effects of the Metal Chelator EDTA and Cinnamaldehyde

The fungal strains used were Lenzites betulina and Laetiporus sulphureus.

EDTA along exhibited strong antifungal activity against Lenzites betulina with antifungal index of 90% at the concentration 50 µg/ml. On the contrary, at the same concentration EDTA revealed very weak antifungal activity against Laetiporus sulphureus with antifungal index of 10%. When the concentration was reduced to 30 µg/ml, EDTA showed a similar inhibitory effect against both *L. betulina* and *L. sulphureus*. EDTA was further tested its combination effect with cinnamaldehyde. When EDTA was used with cinnamaldehyde, the combination performed dramatically better against *L. sulphureus* than either EDTA or cinnamaldehyde along, indicating synergistic effect. However, only additive effect was observed on the combination of EDTA and cinnamaldehyde against *L. betulina*. The results above indicated that the antifungal activities of EDTA were on the extremely two ends. For the fungal strain like *L. sulphureus* which is not effectively inhibited by EDTA, the combination of EDTA with cinnamaldehyde can synergistically enhance the performance and broaden antifungal spectrum as well. Therefore, EDTA is recommended to serve as the additive ingredient into the gallate/fungicide system.

Example 6

Antifungal Activity of Antioxidants (Propyl Gallate and Octyl Gallate) to Inhibit Paper Decay Fungi The fungal strains used were *Aspergillus terreus, Aspergillus niger* and *Chaetomium globosum*.

The test of antifungal activity on paper was based on the rule of CNS 2690 and TAPPI T487 cm-93. The mycelia of fungi strains were transferred to PDA containing Petri dishes respectively. After incubating at 28° C. for 10 days, the spores of fungi were scraped up using platinum thread in laminar flow and put into 10 ml sterile water ($1\times10^5$ CFU/ml), mixing well by shaking, and filtering to get single type spore suspension. The filter paper was cut into 5×5 cm². The chemicals (propyl gallate and octyl gallate) diluted in ethanol were spread on the filter paper. After ethanol evaporating, the filter paper was put on PDA containing Petri dish. 1 ml of spore suspension was evenly spread on the filter paper and incubated for 14 days in an incubator. The antifungal properties of test chemicals were evaluated by observing the growth area of fungi and measuring the percent inhibition ratio of the growth area.

The antifungal activities against paper fungi of test chemicals were shown in Table 7. The inhibition ratio of octyl gallate against *A. terreus* at the concentration of 100 µg/cm² was 51%. When the concentration was raised to be 400 µg/cm², the antifungal activity could reach 94%. The inhibition ratio of octyl gallate against *A. niger* at the concentration of 100 µg/cm² was 72%. When the concentration was raised to be 400 µg/cm², the antifungal activity could reach 99%. As for *C. globosum*, the inhibition ratio of propyl gallate at the concentration of 100 µg/cm² did not show any antifungal activity; however, when the concentration raised to be 400 µg/cm², the antifungal activity reached 100%. On the other hand, the inhibition ratio of octyl gallate against *C. globosum* was 100% at the concentration of 100 µg/cm².

TABLE 7

Percent inhibition ratio of test chemicals against paper fungi at the concentration of 100 µg/cm² and 400 µg/cm²

| Chemicals (µg/cm²) | Fungi | | |
|---|---|---|---|
| | A. terreus | A. niger | C. globosum |
| Propyl gallate (100 µg/cm²) | 0 ± 0 | 0 ± 0 | 0 ± 0 |
| Propyl gallate (400 µg/cm²) | 0 ± 0 | 0 ± 0 | 100 ± 0 |

TABLE 7-continued

Percent inhibition ratio of test chemicals against paper fungi at the concentration of 100 µg/cm² and 400 µg/cm²

| Chemicals (µg/cm²) | Fungi | | |
|---|---|---|---|
| | A. terreus | A. niger | C. globosum |
| Octyl gallate (100 µg/cm²) | 51 ± 4.6 | 72 ± 7.6 | 100 ± 0 |
| Octyl gallate (400 µg/cm²) | 94 ± 8.5 | 99 ± 1.0 | 100 ± 0 |

Example 7

Synergistic Effect of Cinnamaldehyde in Combination with Eugenol on Inhibiting the Growth of *Laetiporus Sulphureus*

Material: Cinnamaldehyde, eugenol and the mixture of cinnamaldehyde and eugenol (cinnamaldehyde:eugenol=20:1, v/v).

The culture medium with concentration 39 g/L were formulated by Potato dextrose agar (PDA) and distilled water. The medium was sterilized under high pressure saturated steam at 121° C. for around 15 min in autoclaves. Fifteen ml medium was added into the culture dish. Test samples were diluted to proper concentration with ethanol. One hundred and fifty µL test sample was mixed with culture medium. After the culture medium was cooled and solidification, it was inoculated with the test sample. The culture medium was put into the incubator (26±2° C., relative humidity 70%). The diameter of growth zone was tested and the antifungal index was calculated when the mycelium of control group fulfilled the dish. Antifungal index formula is as follows.

Antifungal index(AI, %)=(1−Da/Db)×100

Da is the diameter of growth zone in the experimental dish (cm) and Db is the diameter of growth zone in the control dish (cm).

Figure 4:
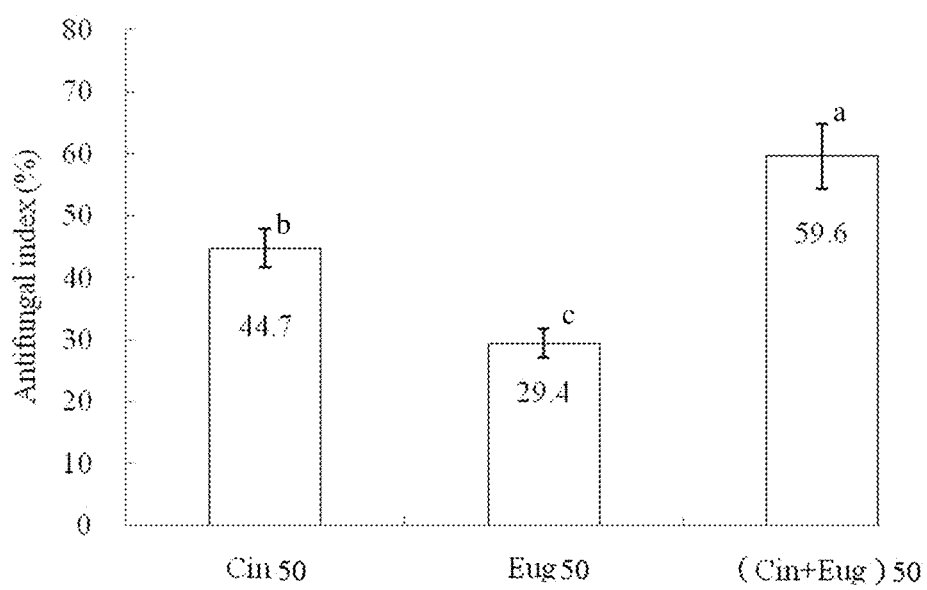
FIG. 4 shows the synergistic effect of 50 µg/mL cinnamaldehyde, eugenol or the mixture of cinnamaldehyde and eugenol on inhibiting the growth of *L. sulphureus*. Cin50: 50 µg/mL cinnamaldehyde; Eug50: 50 µg/mL eugenol; (Cin+Eug)50: the mixture of cinnamaldehyde and eugenol 20:1 (cinnamaldehyde:eugenol=20:1, v/v) under 50 µg/mL concentration. Results are mean±SE. Means in bars with different superscript letters are significant different at alpha level of 0.05.

FIG. 4 showed the activity of cinnamaldehyde, eugenol or the mixture thereof on inhibiting the growth of *Laetiporus sulphureus*. The antifungal index of 50 µg/mL cinnamaldehyde was 44.7%; the antifungal index of 50 µg/mL eugenol was 29.4%; and the antifungal index of the mixture of cinnamaldehyde and eugenol 20:1 (cinnamaldehyde:eugenol 20:1, v/v) at the concentration of 50 µg/mL was 59.6%, which was statistically significant, indicating a synergistic effect.

What is claimed is:

1. A method for inhibition of lignocellulosic material decay caused by *Laetiporus sulphureus* infection, which comprises administering to a lignocellulosic material an effective amount of a composition comprising eugenol and a compound of formula II

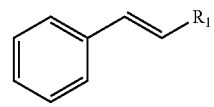

wherein $R_1$ is CHO, wherein the eugenol and the compound of formula II are present at a 1:1 molar ratio, and the concentration of eugenol and the compound of formula II in the composition is from 0.17 to 0.39 mM.

2. The method of claim 1, wherein the lignocellulosic material is an antique made by lignocellulosic materials.

* * * * *